United States Patent [19]

Kühn et al.

[11] Patent Number: 4,961,834

[45] Date of Patent: Oct. 9, 1990

[54] ELECTROCHEMICAL MEASURING CELL FOR AMPEROMETRICALLY DETERMINING AMMONIA AND DERIVATIVES THEREOF

[75] Inventors: Uwe Kühn, Wesenberg; Christiane Roocks, Bad Schwartau; Herbert Kiesele, Lübeck, all of Fed. Rep. of Germany

[73] Assignee: Drägerwerk Aktiengesellschaft, Lübeck, Fed. Rep. of Germany

[21] Appl. No.: 448,269

[22] Filed: Dec. 11, 1989

[30] Foreign Application Priority Data

Dec. 10, 1988 [DE] Fed. Rep. of Germany ....... 3841622

[51] Int. Cl.$^5$ .......................................... G01N 27/31
[52] U.S. Cl. .............................. 204/412; 204/153.14; 204/415
[58] Field of Search ................... 204/415, 412, 153.14

[56] References Cited

U.S. PATENT DOCUMENTS

| 3,649,505 | 3/1972 | Strickler et al. | 204/415 |
| 3,830,718 | 8/1974 | Riseman et al. | 204/415 |
| 3,869,354 | 3/1975 | Montalvo | 204/415 X |
| 4,297,173 | 10/1981 | Hikuma et al. | 204/153.14 X |
| 4,842,697 | 6/1989 | Driscoll et al. | 204/415 X |

Primary Examiner—G. L. Kaplan
Attorney, Agent, or Firm—Walter Ottesen

[57] ABSTRACT

The invention is directed to an electrochemical measuring cell for determining ammonia and its derivatives in a gaseous or liquid measuring sample. The measuring cell has at least one anode and at least one cathode which are disposed in an electrolyte chamber filled with a soluble electrolyte. The electrolyte chamber is closed off in the direction facing toward the measuring sample by a permeable membrane. The measuring cell provides a more selective ammonia sensor having the following advantages: a short response time, a linear response and exhibits the lowest possible tendency toward drift. The electrolyte of the measuring cell is so configured that the reaction products of the measuring reaction do not affect subsequent measurements. For this purpose the measuring cell, which operates in an amperometric measuring mode, contains a soluble non-oxidizable reagent in the electrolyte which reacts completely with ammonia to form an oxidizable product which is convertible by its oxidation into non-oxidizable soluble secondary products which are chemically and electrochemically inert.

10 Claims, 1 Drawing Sheet

Secondary Products

ELECTROCHEMICAL MEASURING CELL FOR AMPEROMETRICALLY DETERMINING AMMONIA AND DERIVATIVES THEREOF

FIELD OF THE INVENTION

The invention relates to an electrochemical measuring cell for determining ammonia and the derivatives thereof in a fluid (gaseous or liquid) measuring sample. The measuring cell has at least one anode and at least one cathode which are arranged in an electrolyte chamber filled with a soluble electrolyte. The electrolyte chamber is closed off with respect to the measuring sample by a permeable membrane.

BACKGROUND OF THE INVENTION

An electrochemical measuring cell of this kind is disclosed in U.S. Pat. No. 3,649,505 and includes a pH-electrode as a measuring electrode which is used to measure hydrogen ions. This potentiometric measurement of the ammonia concentration requires a long time duration for a completed measuring reaction. The long time duration is needed for the adjustment of an equilibrium. In this time duration, the $NH_3$ to be detected and the water content of the electrolyte conjointly form $NH_4OH$ which, in turn, dissociates into $NH_4^+$ ions and $OH^+$ ions. The slow step determining the speed for this reaction is the adjustment of the equilibrium with the gas space.

The concentration of $NH_4^+$ ions is to be held approximately constant in order to carry out an ammonia measurement based on the pH-measurement. This concentration is to be held constant in order to obtain the most linear connection possible between the $NH_3$-partial pressure and the proton concentration to thereby suppress as much as possible disturbances of the pH-value by sources other than the ammonia concentration. For this purpose, an ammonia salt containing $NH_4^+$ is added to the electrolyte of the known measuring cell. In this way, an excess of $NH_4^+$ ions is present in the electrolyte so that with a dissociation of $NH_4OH$ during the ammonia measurement, the $NH_4^+$ ions formed in this way no longer exercise any noticeable influence on the total concentration of $NH_4^+$ ions.

The added ammonia salt thereby makes possible a defined connection between the ammonia concentration to be detected and the $OH^-$ or $H^+$ concentrations for a potentiometric ammonia measurement with the $OH^-$ or $H^+$ concentrations being formed in the electrolyte.

The foregoing notwithstanding, the known measuring cell provides the following disadvantages which are peculiar to the potentiometric measurement.

The glass electrode required for the pH-measurement changes in the characteristic of the glass membrane in the course of its use so that drift phenomena occur.

A stable reference potential is necessary for carrying out the pH measurement and a displacement of this reference potential in the course of use likewise leads to drift phenomena.

The known measuring cell responds to all gases influencing the pH value of the electrolyte so that its selectivity for measurements in corresponding gas mixtures is not adequate. Each potentiometric pH measurement by means of a glass electrode is based on a characteristic which is nonlinear, that is logarithmic. This characteristic must be linearized in a complex manner for obtaining better evaluation possibilities.

SUMMARY OF THE INVENTION

It is an object of the invention to provide an electrochemical measuring cell of the kind described above which is improved so that a selective ammonia sensor is obtained providing the following: short response time, a linear response and a low tendency to drift. It is a further object of the invention to provide such an electrochemical measuring cell having an electrolyte which is so configured that the reaction products of the measuring reaction do not affect subsequent measurements.

The electrochemical measuring cell of the invention is for determining the content of ammonia and the derivatives thereof in a fluid measuring sample. The measuring cell includes: a housing having an opening directed toward the sample to be measured and defining an electrolyte chamber; a permeable membrane mounted on the housing for closing off the chamber; an anode and a cathode disposed in the chamber so as to be in spaced relationship to each other; and, a non-oxidizable soluble reagent contained in the electrolyte for completely reacting with ammonia while forming oxidizable products which oxidize into soluble chemically and electrochemically inert secondary products.

The advantage of the invention is especially that the ammonia, which is oxidizable only with difficulty, is not directly converted, that is, it must not be oxidized at the measuring electrode; instead, an initial equilibrium reaction of the ammonia with a non-oxidizable reagent leads to a complete conversion of the ammonia into easily oxidizable products and these products are converted at the measuring electrode.

By dividing the cell reaction into two individual reaction steps (namely, the initial equilibrium reaction and the actual cell reaction), the condition is obtained that a cell reaction takes place which is selective for ammonia and its derivatives such as amine or hydrazine and this cell reaction is amperometrically detectable. The amperometric ammonia determination is only made possible by the features according to the invention. An amperometric ammonia determination cannot be used in known measuring cell since only an exchange of the $NH_4^+$ ions in the electrolyte would take place for the reaction of $NH_3$ so that the molar ratio would remain the same and there would be no contribution to a resulting measuring signal.

An ammonia salt is preferably selected as a suitable reagent which forms an amine with the ammonia. The total measuring reaction then takes place in two individual steps of which the first step provides that the ammonia diffusing through the membrane into the electrolyte reacts with the organic ammonium salt to form ammonium ion and an organic oxidizable amine. This acid-base equilibrium is in advance of the actual detection reaction and lies completely on the side of the amine formation since the organic ammonium salt is present in a high excess and its acidity is greater than that of the ammonium salt which is formed. With this initial equilibrium, the total ammonia which diffuses from the measuring sample into the electrolyte through the membrane is immediately converted so that a high concentration gradient of ammonia results in the electrolyte behind the membrane and the measuring cell thereby exhibits a rapid response time and a high measuring sensitivity. The organic amine formed hereby is oxidized itself at the measuring electrode instead of the ammonia whereby reaction products result which disturb neither the transport of the ammonium nor the oxidation of the organic amine at the measuring electrode. The oxidation of the organic amine to a radical cation occurs more rapidly and at a lower potential than the oxidation of the ammonia itself. The cell measuring current generated by the oxidation is applied as a measure for the ammonia concentration in the measuring sample. In this way, a measuring cell is obtained having a lower cross sensitivity on other components present in the measuring sample as would be the case for a direct ammonia oxidation and a linear connection between the ammonia concentration and the measuring current is obtained.

Advantageously, the electrolyte comprises zwitterionic buffering substances which are also known as Good buffers. These water-soluble buffer substances are not toxic and, at the same time, have a double function as electrolyte and reagent.

An especially excellent buffer substance is the hydrochloride of trishydroxymethylaminomethane which is known under the abbreviated designation TRIS-HCl. A measuring cell having such an electrolyte exhibits a short signal rise time since the protonation of the ammonia occurs rapidly and completely and the subsequent oxidation of the released amine takes place with adequate speed. The secondary products which occur have no disturbing influence on the ammonia diffusing into the measuring cell and on the oxidation of the released amine. For this reason, stable signals are obtained even during measurements of longer duration. Furthermore, the TRIS-HCl is excellently water soluble, approximately up to 2 molar, so that a more than adequate electrolyte supply can be provided in a measuring cell without making the constructive volume thereof unnecessarily large.

It is advantageous to provide the electrolyte with a hygroscopic additive to delay a premature drying up of the electrolyte. Such an additive can advantageously be tetramethylammoniumchloride (2-molar) or also lithiumchloride (2-molar).

A measuring electrode made of amorphous gold sintered with PTFE (polytetrafluoroethylene) powder and a rhodium additive appears to be the most advantageous in order to obtain the fastest possible oxidation of the released amine and a reduced sensitivity with respect to oxidizable gases such as CO and $H_2$.

In the event that a reference electrode is utilized for stabilizing the operating point, an especially good stability is obtained when the reference and counter electrodes are made of iridium with sintered PTFE. These electrodes exhibit also a good insensitivity with respect to hydrogen.

A sintering with polypropylene in lieu of polytetrafluoroethylene provides the further advantage that ammonia is stored to a lesser extent in polypropylene.

A reaction example is illustrated below with respect to TRIS-HCl as the electrolyte.

In an acid-base reaction taking place ahead of the detection reaction, the ammonia reacts with the TRIS-HCl to form an ammonium ion and the organic amine of TRIS-HCl corresponding thereto. Since the equilibrium reaction lies completely on the right side of the reaction equation, the maximum stoichiometrical number of organic amines is obtained which are oxidized in the secondary reaction at the measuring electrode. The electron released by the oxidation of the amine contributes to the measuring-cell current. The organic amine oxidized to a radical cation decomposes into further reaction products which, however, neither disturbingly influence the equilibrium reaction nor the oxidation step.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
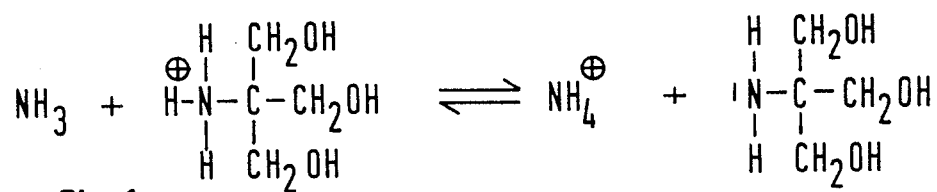
FIG. 1 illustrates the equilibrium reaction which takes place in advance of the oxidation.
Figure 2:
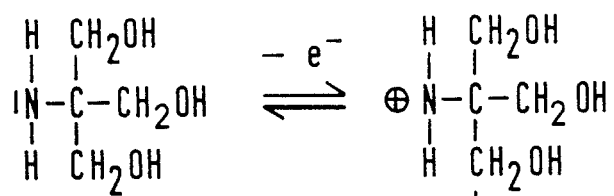
FIG. 2 shows how the subsequent oxidation takes place.
Figure 3:
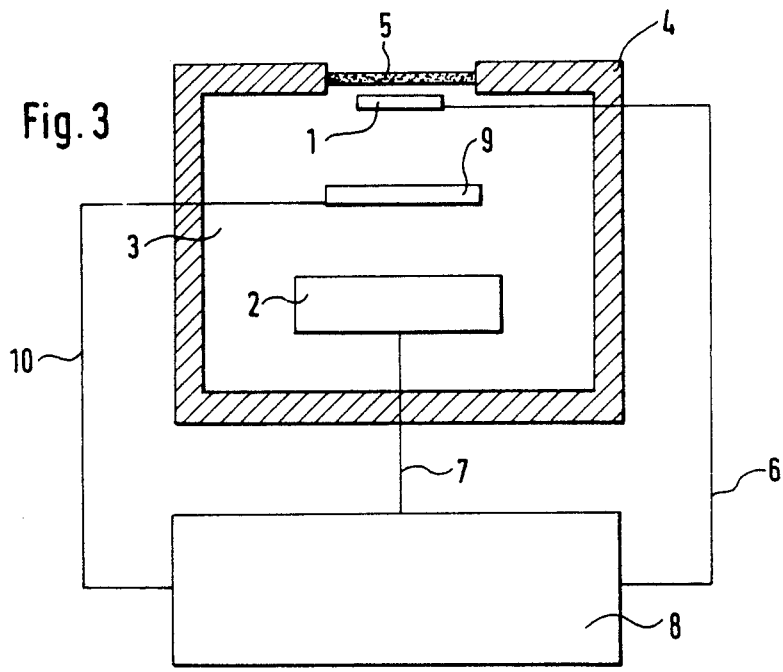
FIG. 3 is a side elevation view, in section, of a measuring cell according to an embodiment of the invention.

An embodiment of an electrochemical measuring cell provided with the electrolyte is shown in FIG. 3. The measuring cell includes an anode 1, a cathode 2 and a reference electrode 9 which are arranged in an electrolyte chamber 3 of the measuring cell housing 4. The electrolyte chamber 3 is filled with an aqueous solution of TRIS-HCl. The electrolyte chamber 3 is closed off in a direction facing toward the measuring sample by a permeable membrane 5. The anode 1, the cathode 2 and the reference electrode 9 all have connecting leads (6, 7, 10) which pass through the housing 4 and are connected to an evaluation unit 8 for further processing of the measuring signal.

It is understood that the foregoing description is that of the preferred embodiments of the invention and that various changes and modifications may be made thereto without departing from the spirit and scope of the invention as defined in the appended claims.

What is claimed is:

1. An electrochemical measuring cell for determining the content of ammonia and the derivatives thereof in a fluid measuring sample, the measuring cell comprising:
   a housing having an opening directed toward the sample to be measured and defining an electrolyte chamber;
   a permeable membrane mounted on said housing for closing off said chamber;
   an anode and a cathode disposed in said chamber so as to be in spaced relationship to each other; and,
   a non-oxidizable soluble reagent contained in said electrolyte for completely reacting with ammonia while forming an oxidizable product which oxidizes into non-oxidizable, soluble, chemically and electrochemically inert secondary products.

2. The electrochemical measuring cell of claim 1, said reagent being an organic ammonium salt which reacts with ammonia to form an amine.

3. The electrochemical measuring cell of claim 1, said electrolyte containing a zwitterionic buffer (Good buffer).

4. The electrochemical measuring cell of claim 1, said reagent being trishydroxymethylaminomethanehydrochloride (TRIS-hydrochloride).

5. The electrochemical measuring cell of claim 1, said electrolyte including a hygroscopic additive.

6. The electrochemical measuring cell of claim 5, said hygroscopic additive being an additive selected from the group consisting of tetramethylammoniumchloride and lithiumchloride.

7. The electrochemical measuring cell of claim 1, said measuring electrode comprising amorphous gold containing rhodium and sintered with PTFE powder as a hydrophobic binding agent.

8. The electrochemical measuring cell of claim 1, said measuring electrode comprising amorphous gold containing rhodium and sintered with polypropylene powder as a hydrophobic binding agent.

9. The electrochemical measuring cell of claim 1, said reference electrode and said counter electrode being made of sintered iridium finely distributed in PTFE as a hydrophobic binding agent.

10. The electrochemical measuring cell of claim 1, said reference electrode and said counter electrode being made of sintered iridium finely distributed in polypropylene as a hydrophobic binding agent.

* * * * *